US00PP25026P2

(12) United States Plant Patent
Brea

(10) Patent No.: US PP25,026 P2
(45) Date of Patent: Nov. 4, 2014

(54) ***DIANTHUS* PLANT NAMED 'BREAGREEN'**

(50) Latin Name: *Dianthus barbatus*
Varietal Denomination: Breagreen

(71) Applicant: Ezio Brea, Sanremo (IT)

(72) Inventor: Ezio Brea, Sanremo (IT)

(73) Assignee: Brea Ezio I.I, Sankeme (IT)

( * ) Notice: Subject to any disclaimer, the term of this patent is extended or adjusted under 35 U.S.C. 154(b) by 8 days.

(21) Appl. No.: 13/815,649

(22) Filed: Mar. 13, 2013

(51) Int. Cl.
*A01H 5/00* (2006.01)

(52) U.S. Cl.
USPC ..... Plt./272

(58) Field of Classification Search
USPC ..... Plt./272, 273
See application file for complete search history.

*Primary Examiner* — Kent L Bell
(74) *Attorney, Agent, or Firm* — C. A. Whealy

(57) ABSTRACT

A new and distinct cultivar of *Dianthus* plant named 'Breagreen', characterized by its upright plant habit; strong and thick flower stems; large flowers with numerous bright green-colored bracts; and good postproduction longevity.

1 Drawing Sheet

Botanical designation: *Dianthus barbatus.*
Cultivar denomination: 'BREAGREEN'.

BACKGROUND OF THE INVENTION

The present invention relates to a new and distinct cultivar of *Dianthus* plant, botanically known as *Dianthus barbatus*, grown commercially as cut flower and hereinafter referred to by the name 'Breagreen'.

The new *Dianthus* plant is a naturally-occurring whole plant mutation of *Dianthus barbatus* 'Hilbrequeen', not patented. The new *Dianthus* plant was discovered and selected by the Inventor as a single flowering plant from within a population of plants of 'Hilbrequeen' in a controlled greenhouse environment in Sanremo, Italy in May, 2008.

Asexual reproduction of the new *Dianthus* plant by terminal cuttings propagated in a controlled greenhouse environment in Sanremo, Italy since September, 2008 has shown that the unique features of this new *Dianthus* plant are stable and reproduced true to type in successive generations of asexual reproduction.

SUMMARY OF THE INVENTION

Plants of the new *Dianthus* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Breagreen'. These characteristics in combination distinguish 'Breagreen' as a new and distinct *Dianthus* plant:

1. Upright plant habit.
2. Strong and thick flower stems.
3. Large flowers with numerous bright green-colored bracts.
4. Good postproduction longevity.

Plants of the new *Dianthus* differ from plants of the parent, 'Hilbrequeen', primarily in flower form as plants of 'Hilbrequeen' have normal floral structure and dark red-colored petals.

Plants of the new *Dianthus* can be compared to plants of *Dianthus barbatus* 'Temarisou', not patented. In side-by-side comparisons conducted in De Kwakel, The Netherlands, plants of the new *Dianthus* differed from plants of 'Temarisou' in the following characteristics:

1. Plants of the new *Dianthus* had thicker flower stems than plants of 'Temarisou'.
2. Plants of the new *Dianthus* had longer and broader leaves than plants of 'Temarisou'.
3. Plants of the new *Dianthus* produced fewer flowering stems than plants of 'Temarisou'.

BRIEF DESCRIPTION OF THE PHOTOGRAPH

The accompanying photograph illustrates the overall appearance of the new *Dianthus* plant showing the colors as true as it is reasonably possible to obtain in colored reproductions of this type. Colors in the photograph may differ slightly from the color values cited in the detailed botanical description which accurately describe the colors of the new *Dianthus* plant.

The photograph comprises a side perspective view of a typical flowering stem of 'Breagreen'.

DETAILED BOTANICAL DESCRIPTION

Plants used in the aforementioned photograph and following observations and measurements describe plants grown during the autumn in ground beds in a glass-covered greenhouse in De Kwakel, The Netherlands and under cultural practices typical of commercial cut flower *Dianthus* production. During the production of the plants, day temperatures ranged from 16° C. to 25° C. and night temperatures ranged from 12° C. to 18° C. Plants were pinched one time about four weeks after planting. Plants were 20 weeks old when the photograph was taken and 24 weeks old when the description was taken. In the following description, color references are made to The Royal Horticultural Society Colour Chart, 2007 Edition, except where general terms of ordinary dictionary significance are used.

Botanical classification: *Dianthus barbatus* 'Breagreen'.

Parentage: Naturally-occurring whole plant mutation of *Dianthus barbatus* 'Hilbrequeen', not patented.

Propagation:

*Type*.—By terminal cuttings.

*Time to initiate roots, summer*.—About seven days at 20° C. to 25° C.

*Time to initiate roots, winter*.—About eight days at 18° C.

*Time to produce a rooted young plant, summer*.—About four weeks at 20° C. to 25° C.

*Time to produce a rooted young plant, winter*.—About five weeks at 18° C.

*Root description*.—Medium in thickness, fibrous; white in color.

*Rooting habit*.—Moderate branching; medium density.

Plant description:

*Plant and growth habit*.—Herbaceous perennial; upright plant form with strong flowering stems; narrow inverted triangle; moderately vigorous growth habit.

*Flowering stem production*.—Basal-branching growth habit; when pinched, about twelve flowering stems develop per plant per year.

*Plant height*.—About 71.5 cm.

*Plant diameter or spread*.—About 40 cm.

*Flowering stems*.—Length: About 64.7 cm. Diameter: About 5 mm; at the nodes, about 6 mm. Internode length: About 2.5 cm to 7.5 cm. Strength: Strong. Texture: Smooth, glabrous. Color: Close to 144A; at the nodes, close to between 144B and 145A.

*Leaf description*.—Arrangement: Opposite, simple; sessile. Length: About 17.3 cm. Width: About 2.7 cm. Shape: Oblanceolate. Apex: Acute. Base: Long cuneate, decurrent. Margin: Finely serrate. Texture, upper and lower surfaces: Smooth, glabrous; slightly rugose. Venation pattern: Pinnate. Color: Developing leaves, upper surface: Close to 143A. Developing leaves, lower surface: Close to 143C. Fully expanded leaves, upper surface: Close to N137C; venation, close to 143B. Fully expanded leaves, lower surface: Close to 147B; venation, close to 144A.

Flower description:

*Flower type and flowering habit*.—Single rotate terminal flowers without floral structures typical of *Dianthus* plants; flower head covered with modified bracts.

*Natural flowering season*.—Flowering is continuous through the summer into the autumn in The Netherlands; plants begin flowering about 14 weeks after planting. Flower longevity: Good postproduction longevity with flowers lasting about 14 to 20 days as cut flowers; flowers persistent.

*Flower diameter*.—About 9.1 cm.

*Flower depth* (*height*).—About 6.8 cm.

*Petals*.—None observed.

*Sepals*.—None observed.

*Reproductive organs*.—None observed.

*Fruits and seeds*.—None observed.

*Bracts*.—Quantity per flower: About 40. Length: About 2 cm. Width: About 1.5 cm. Shape: Lanceolate. Apex: Long acuminate. Base: Cuneate. Margin: Entire. Texture, upper and lower surfaces: Smooth, glabrous. Color: When opening, upper and lower surfaces: Close to 143C. Fully opened, upper and lower surfaces: Close to 137C; color does not change with subsequent development.

Disease & pest resistance: Plants of the new *Dianthus* have not been observed to be resistant to pathogens and pests common to *Dianthus* plants.

Temperature tolerance: Plants of the new *Dianthus* have been observed to tolerate high temperatures about 35° C. and to be hardy to USDA Hardiness Zone 5.

It is claimed:

1. A new and distinct *Dianthus* plant named 'Breagreen' as illustrated and described.

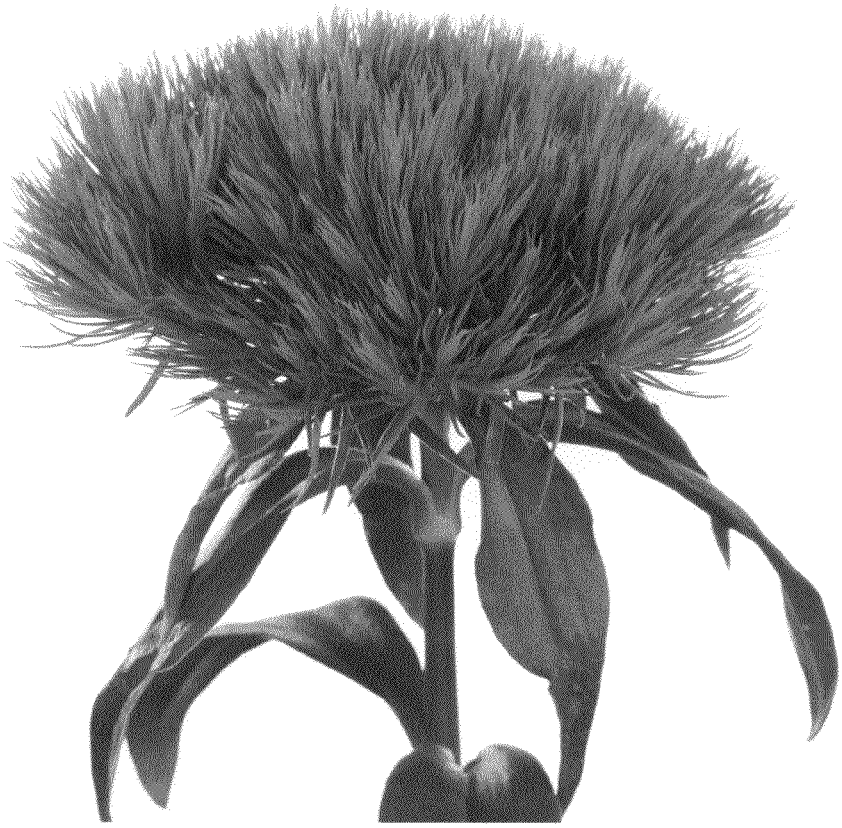

* * * * *